(12) United States Patent
Cole (10) Patent No.: US 11,097,074 B2
(45) Date of Patent: Aug. 24, 2021

(54) INHALANT DELIVERY APPARATUS, SYSTEM AND METHOD

(71) Applicant: Maury D. Cole, San Diego, CA (US)

(72) Inventor: Maury D. Cole, San Diego, CA (US)

( * ) Notice: Subject to any disclaimer, the term of this patent is extended or adjusted under 35 U.S.C. 154(b) by 168 days.

(21) Appl. No.: 16/207,049

(22) Filed: Nov. 30, 2018

(65) Prior Publication Data

US 2019/0167922 A1 Jun. 6, 2019

Related U.S. Application Data

(60) Provisional application No. 62/593,505, filed on Dec. 1, 2017.

(51) Int. Cl.

| | |
|---|---|
| *A61M 11/04* | (2006.01) |
| *G16H 20/13* | (2018.01) |
| *G05B 19/042* | (2006.01) |
| *A61M 11/00* | (2006.01) |
| *A61M 15/06* | (2006.01) |
| *A24F 40/30* | (2020.01) |
| *A24F 40/44* | (2020.01) |

(Continued)

(52) U.S. Cl.
CPC ........... *A61M 11/041* (2013.01); *A24F 40/30* (2020.01); *A24F 40/44* (2020.01); *A24F 40/48* (2020.01); *A24F 40/50* (2020.01); *A24F 40/65* (2020.01); *A61M 11/007* (2014.02); *A61M 15/06* (2013.01); *G05B 19/0428* (2013.01); *G16H 20/13* (2018.01); *A24F 40/10* (2020.01); *A61M 2202/04* (2013.01); *A61M 2205/14* (2013.01); *A61M 2205/3553* (2013.01); *A61M 2205/3584* (2013.01); *A61M 2205/50* (2013.01); *G05B 2219/24015* (2013.01)

(58) Field of Classification Search
CPC ........ A24F 47/008; A24F 40/44; A24F 40/65; A24F 40/50; A24F 40/48; A24F 40/30; A24F 40/10; A61M 11/041; A61M 11/007; A61M 15/06; A61M 2205/50; A61M 2205/3553; A61M 2205/14; A61M 2205/3584; A61M 2205/52; A61M 15/0021; A61M 2205/581; G16H 20/13; G16H 40/67; G05B 19/0428; G05B 2219/24015

See application file for complete search history.

(56) References Cited

U.S. PATENT DOCUMENTS

| | | | | |
|---|---|---|---|---|
| 2011/0290269 | A1* | 12/2011 | Shimizu ................. | A24F 40/46 131/330 |
| 2012/0227753 | A1* | 9/2012 | Newton ................. | A24F 15/18 131/347 |

(Continued)

*Primary Examiner* — Victoria Murphy
(74) *Attorney, Agent, or Firm* — Procopio, Cory, Hargreaves & Savitch LLP (57) ABSTRACT

The present disclosure relates to an inhalant delivery apparatus to a control system and method for controlling delivery of vapor from the apparatus to a user. The apparatus comprises a vaporization device or box which has an inlet with a seat for receiving an end portion of a separate mouthpiece or combined mouthpiece and wick designed for releasable attachment to the box outlet. The control system controls dispensing of a dose via the vaporizer device and mouthpiece by controlling the timing and amount of medication in the delivered dose, and requires specific input from the user before a dose is dispensed.

10 Claims, 10 Drawing Sheets

(51) Int. Cl.
*A24F 40/48* (2020.01)
*A24F 40/50* (2020.01)
*A24F 40/65* (2020.01)
*A24F 40/10* (2020.01)

(56) References Cited

U.S. PATENT DOCUMENTS

| | | | |
|---|---|---|---|
| 2013/0276799 A1* | 10/2013 | Davidson | A61M 15/0045 131/273 |
| 2016/0007652 A1* | 1/2016 | Taluskie | A61M 11/041 131/328 |
| 2016/0143361 A1* | 5/2016 | Juster | A24F 40/65 392/404 |
| 2017/0035116 A1* | 2/2017 | Batista | A24F 40/46 |
| 2017/0172212 A1* | 6/2017 | Phillips | A24F 47/008 |
| 2017/0196270 A1* | 7/2017 | Vick | H02J 7/0042 |
| 2017/0303590 A1* | 10/2017 | Cameron | G01P 5/02 |
| 2018/0043114 A1* | 2/2018 | Bowen | A61M 15/003 |

* cited by examiner

INHALANT DELIVERY APPARATUS, SYSTEM AND METHOD

CROSS-REFERENCE TO RELATED APPLICATIONS

The present application claims priority to U.S. Provisional Patent App. No. 62/593,505, filed on Dec. 1, 2017, which is hereby incorporated herein by reference as if set forth in full.

BACKGROUND

1. Field of the Invention

The present disclosure relates to an inhalant delivery apparatus, system and method and is particularly concerned with an apparatus, system, and method in which a vapor such as a medicinal vapor is produced from one or more substances and dispensed to a nozzle or mouthpiece for inhaling by a user, and with a medication delivery control system and method for remotely controlling the dispensing of a prescribed dose of vaporized medication and carrier liquid.

2. Related Art

Medication inhalers are well known in the medical field for treatment of various conditions by inhaling doses of medication such as drugs for relieving asthma and other respiratory diseases. Such devices provide metered doses of aerosolized medications from a pressurized canister. So-called vape devices are also known for inhalation of flavored liquids for recreational purposes, such as electronic cigarettes or the like. An electronic cigarette is a handheld device containing a liquid which is atomized by a heating element and dispensed as an aerosol via a mouthpiece. The liquid may be a mixture of nicotine or nicotine substitutes and other liquids such as water, ethylene glycol, and flavorings.

Drug addicts are often treated for drug dependence using a substitute medication, such as methadone for opioid addiction. Such substitutes must be administered under monitored, highly controlled conditions. This can be time consuming for both physician and patient.

SUMMARY

Provided herein is a medicinal inhalant delivery apparatus or device, and a delivery control system and method which allows remote control of medication delivery by a physician. The inhalant delivery or vaporization apparatus dispenses a physician controlled dose of vaporized medication to a mouthpiece either one time or at physician controlled intervals. In some embodiments, the inhalant delivery apparatus or device may be similar to an electronic vaporizer (also known as an e-cigarette when used for delivery of tobacco or the like) or mod box and is associated with a control system and method for controlling delivery of vapor from the device to a user. In one embodiment, the vaporizer apparatus comprises an electronic vaporization (or vape) unit comprising an outer container or housing containing an input/output communication device or module for communication with a remote medication delivery control system or server for controlling operation of the vaporization unit, a vaporization control signal processor in communication with the input/output communication device, and a separate mouthpiece device configured for releasable attachment in an output port or seat of the housing. In one embodiment, the separate mouthpiece device is a mouthpiece only and a replaceable wick is mounted in the housing in communication with the outlet port. In other embodiments, the mouthpiece device is a combined mouthpiece and wick designed for releasable engagement in a seat communicating with the outlet port when the device is attached to the housing. In one embodiment, at least two liquid tanks are located in the housing and are configured to supply selected amounts of the liquids to the wick via first and second supply passageways for vaporization on receipt of a vaporization control signal when the mouthpiece device is secured at the outlet port and the apparatus is linked to the remote medication delivery control system. In one embodiment, the vaporization control signal actuates pumps to supply measured amounts of the two liquids to the heated wick. In another embodiment, a combined mouthpiece and wick device is a one-time use disposable device which contains a wick which is pre-loaded with medication to be vaporized, and the vaporization control signal actuates a heating element associated with the wick in order to vaporize the medication.

The medication delivery control system controls dispensing of a dose from the electronic vape box or vaporization unit by controlling the timing and amount of medication in the delivered dose, and requires the user to log-in to the system and answer questions before a dose is dispensed.

In some embodiments, a wick is mounted in the housing outlet port or seat and the heating element is associated with the wick. In some embodiments, the wick is located in the mouthpiece and engages in a seat at the container outlet when the mouthpiece is attached to the container. In some embodiments, the mixture of liquids to be vaporized is delivered to the wick from tanks inside the container. In some embodiments, the wick is preloaded with the mixture to be vaporized. In some embodiments, a tracking device such as a GPS tracker is associated with the container. In some embodiments, engagement of the mouthpiece device with the vaporization unit simultaneously opens shutters in liquid inlet ports of the seat to allow liquid supply to the wick, and the shutters are biased back into a closed and sealed condition when the mouthpiece device is removed from the vaporization unit.

In various embodiments, the inhalant delivery apparatus comprises at least two tanks inside the housing containing selected first and second liquids and the mouthpiece device and housing outlet port or seat inside the port have mateable connecting formations such as screw threads or other fasteners configured for releasable attachment of the mouthpiece device to the housing. The mouthpiece device in some embodiments is movable between a locked and released condition relative to the housing. The apparatus in some embodiments further comprises a vaporizer such as a heating element for vaporizing a predetermined amount of medication from the tanks and supplying the vaporized medication to the output, and a remotely operable actuator for controlling supply of predetermined amounts of the first and second liquids to a wick located in the housing or in the mouthpiece device and actuating the vaporizer or heating element to provide the vaporized medication output to the mouthpiece.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

The present disclosure generally relates to an apparatus, system and method for administering medication and which may be used in one example for administering drug substitutes such as methadone to recovering addicts. In some embodiments, an inhalant delivery apparatus or device which operates in a similar manner to an e-vape or electronic cigarette is remotely controlled by a physician or the like to deliver a determined amount of medication at predetermined time intervals. In some embodiments, the dose can only be delivered when a mouthpiece is secured to an outlet port of a box or container which contains supplies of the medication and a carrier. Once the dose is delivered, the box outlet is locked and no further medication can be delivered until expiry of a predetermined time period.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention.

Figure 1:
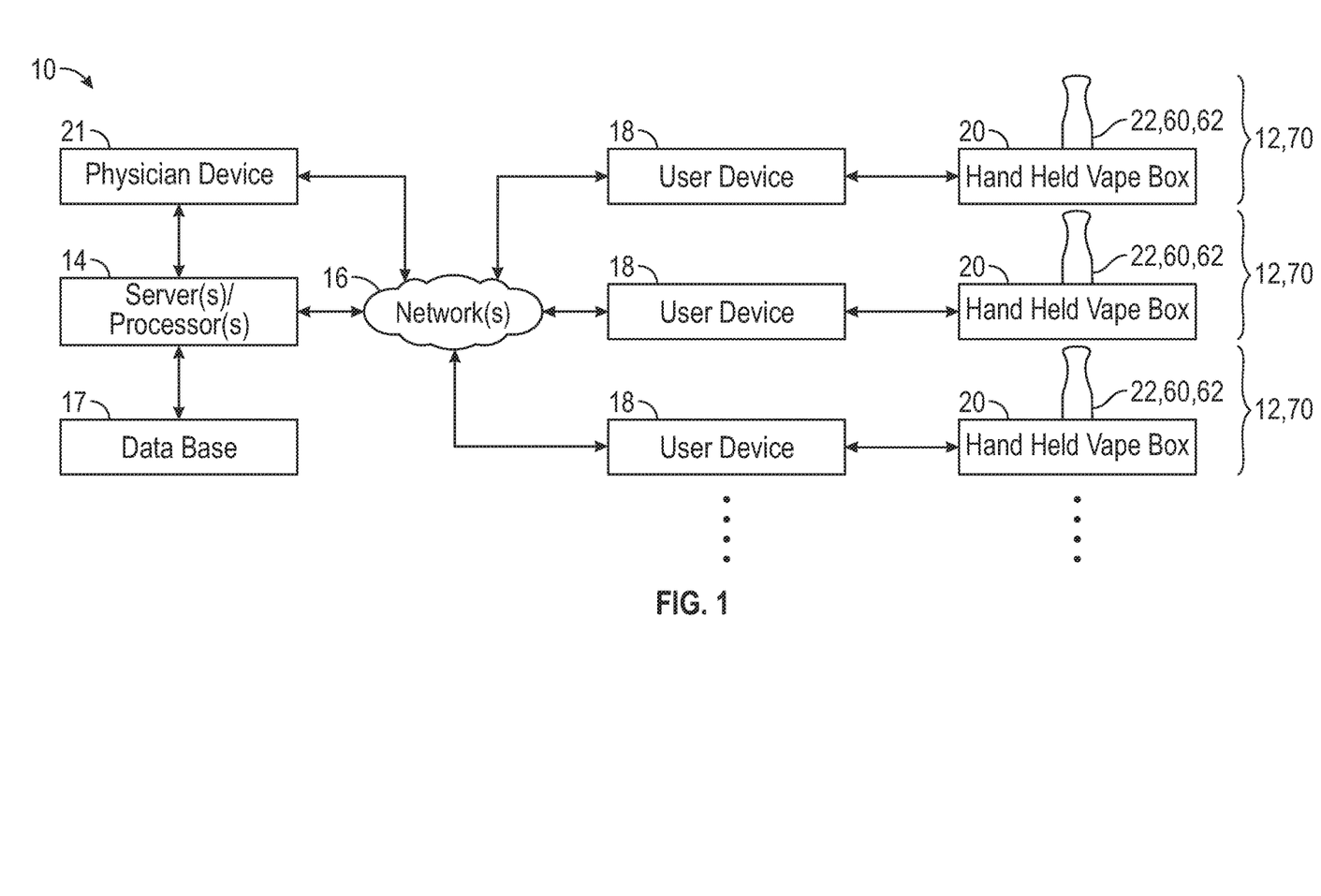
FIG. 1 is a block diagram illustrating one embodiment of an inhalant delivery system for controlled delivery of a medication to one or more patients as an inhalable vapor.

FIG. 1 illustrates one embodiment of a web or network-based operating system 10 for controlling operation of a plurality of inhalant delivery devices or electronic vaporization (or "vape") assemblies 12 or 70 as described in more detail below, to deliver measured doses of medication to patients at predetermined time intervals. System 10 in some embodiments may comprise a computer or remote processing device or server 14 which may be remotely or locally associated with a medical facility and which is in communication with one or more inhalant delivery devices or electronic vaporization assemblies 12 or 70 via one or more public or private networks 16. Each inhalant delivery device or electronic vaporization assembly 12, 70 includes an electronic vaporization unit 20 and a separate mouthpiece device 22, 60 or 62. The electronic vaporization unit 20 is connected by the patient to a local user device or processor 18 such as a laptop or other computer or a mobile communication device via a wired connection such as a USB cord or a wireless connection (such as Bluetooth® or the like), and the patient then logs in to a software application ("App") for their medication delivery, as described in more detail below in connection with FIG. 10. Physicians or other medical personnel log in to the app via their mobile phone, laptop or other computer device 21. This allows the physician or automated delivery control system to obtain any necessary information from the patient and if appropriate to actuate delivery device or vaporization apparatus 12 or 70 to deliver a physician determined dose of vaporized medication to a mouthpiece 22, 60, 66 of apparatus 12 or 70, as described in more detail below.

Figure 2:
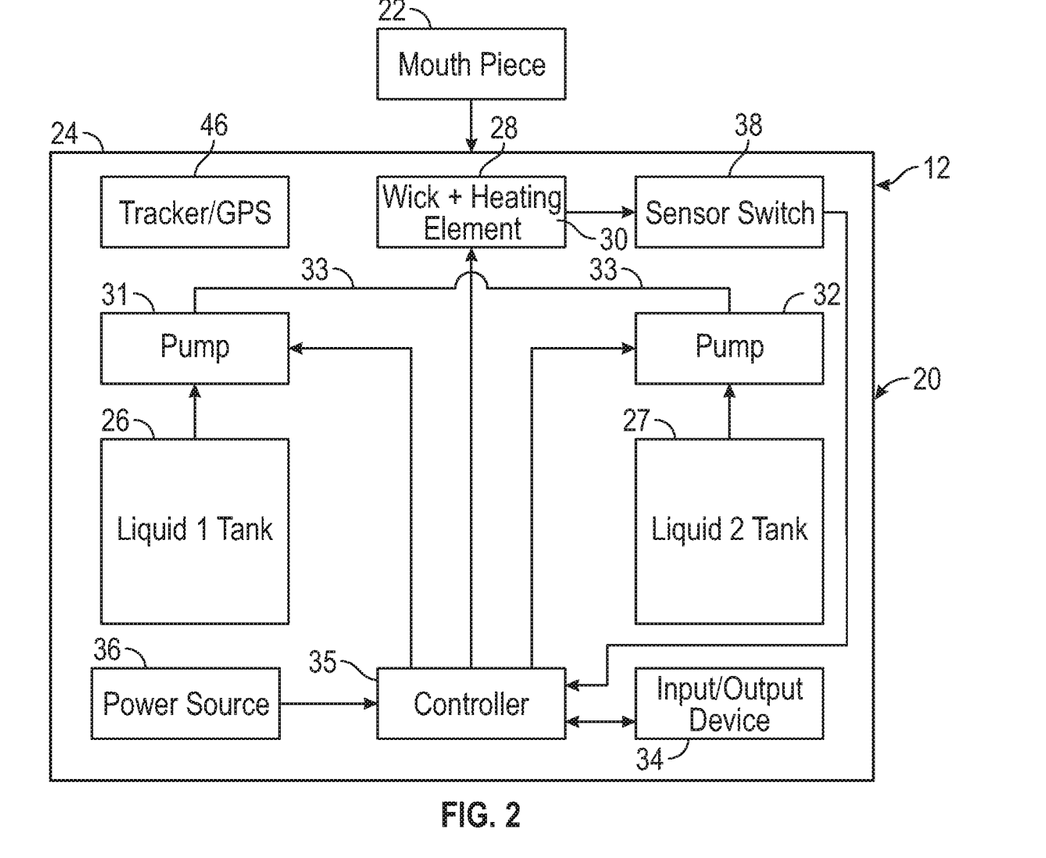
FIG. 2 is a block diagram which illustrates one embodiment of a vaporized medication or inhalant delivery apparatus with a removable mouthpiece, for use in the system of FIG. 1.
Figure 3:
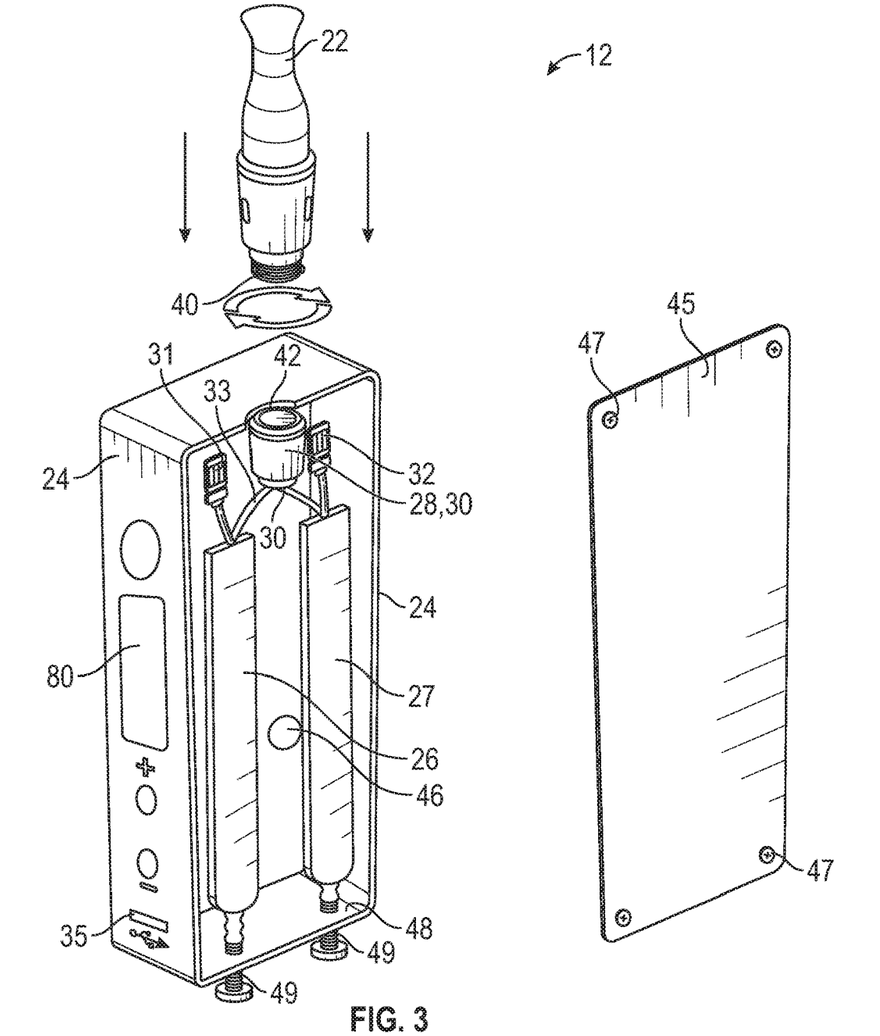
FIG. 3 is a perspective view of one embodiment of the inhalant delivery or e-vape apparatus of FIG. 2 with the cover plate of the container or box removed to reveal the internal components.

FIGS. 2 and 3 illustrate one embodiment of a hand held inhalant delivery device or electronic vaporization apparatus or assembly 12 designed for use in the system of FIG. 1. Apparatus 12 comprises electronic vaporization unit 20 and a separate mouthpiece 22 which is releasably securable to the outlet port 42 or seat of the vaporization unit via a twist lock arrangement described in more detail below. In some embodiments, vaporization unit 20 comprises an outer housing or container 24 which contains two metered holding tanks 26, 27, one tank 26 containing a medication in liquid form such as methadone which is used by recovering drug addicts, and the other tank 27 containing a vehicle or carrier liquid for mixing with the medication prior to vaporization. A conventional wick and heating element 28, 30 are located in a seat in communication with outlet port 42 of container 24, and liquid pumps 31, 32 are connected to the respective tanks to supply a measured amount of liquid via delivery tubes or supply passageways 33 to ports in the seat which communicate with the wick. Shutters or one way valves shut off the connection from the tanks to the wick when mouthpiece device 22 is detached from the housing as in FIG. 3, as explained in more detail below.

Vaporization unit 20 also comprises an input/output communication device 34 and a controller or control signal processing unit 35 which is in communication with I/O device 34. Power source 36 such as a battery supplies power to the electronic components, and a sensor or switching device 38 may optionally be associated with the seat or outlet port to detect when the mouthpiece 22 is secured in the port 42 and communicating with the wick 28, 30. As illustrated in FIG. 3, in one embodiment the mouthpiece 22 has a threaded connecting or fastener portion 40 designed for threaded engagement in a matching threaded or fastener portion of a seat or outlet port 42 which communicates with wick 28. Connecting portion 40 is inserted into the threaded portion of the outlet and rotated into a locked or secured position (which may be identified by an audible click or the like). It is only when the mouthpiece is secured in place that vaporized medication can be delivered to the mouthpiece, as described in more detail below in connection with FIGS. 8A to 9B. Actuation of the fluid supply pumps 31, 32 to supply preselected amounts of liquids to the wick is remotely controlled by processing system 14 based on detection of the connected mouthpiece device as well as physician and user inputs and the time since the last dose was delivered. Once delivery of the prescribed dose is completed, the device is turned off, a timer is started, and the device is not activated again until the end of a prescribed time period to the next dose.

After the first dose of inhaled medication, the existing wick may be re-used for the next dose, or may be replaced by a lab technician or medical personnel at a clinic. The hand held vaporization device 12 of FIGS. 2 and 3 is therefore mainly intended for use by the patient during daily visits to a clinic during a preliminary dose adjustment period by the doctor. Once the optimum initial dose has been determined, one of the alternative devices of FIGS. 4 to 9B may be provided to a patient for use at a clinic, in a home environment or elsewhere, as described in more detail below. Doses may be prescribed at 24 hour periods (once a day) or at more frequent intervals, depending on the type of medication.

Figure 3A:
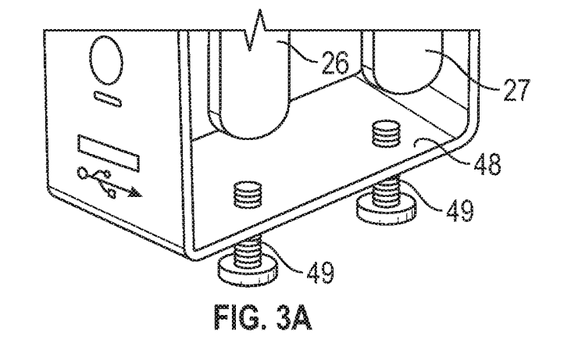
FIG. 3A is a broken away view of a bottom portion of the delivery housing of FIG. 3 illustrating the tank refill tubes separated from the liquid holding tanks either for maintenance purposes or as a result of tampering.

In some embodiments, housing 24 is a generally rectangular container or box with a front cover plate 45, as illustrated in FIG. 3. The front cover is removable by authorized personnel for maintenance purposes via tamper proof keyed locking screws 47 or other secure locking fastener mechanisms. A GPS or other tracker device 46 may be mounted inside the box. In some embodiments, holding tanks 26 and 27 are re-fillable via lockable fill ports or supply tubes 49 which extend through the lower wall of the box and are threadably or otherwise engaged in fill ports (not visible) in tanks 26 and 27, as seen in FIG. 3. In some embodiments, an absorbent pad 48 may be mounted in the lower end of housing or container 24. In the event that anyone tries to remove supply tubes 49 to gain access to the contents of tank 26 or 27, as seen in FIG. 3A, liquid leaks from the tanks via the open fill ports. Thus, if a user attempts to gain access to the drug via the supply tube inlets, liquid from both tanks is automatically expelled and absorbed by pad 48. Any suitable pad for absorbing liquids may be used, such as a DriMop® Liquid Absorber as manufactured by Multisorb Technologies, Inc. of Buffalo, N.Y., USA. Any minor leakage is also absorbed by pad 48.

In some embodiments, each holding tank is a graduated cylinder with a plunger at the bottom which is actuated via pump 31 or 32 to expel a predetermined amount of liquid from the tank onto the wick. In order to use the hand held medication delivery device or vape box 12, a patient or individual undergoing treatment first secures mouthpiece 22 in the box outlet or connecting portion 42 until it is locked in place, opening valves or shutters at the inlets of supply tubes 33 for communication with internal wick 32. The mouthpiece must be in the proper position before a dose of medication is delivered. The patient is also required to connect device 12 to a suitable processing device such as a laptop or desk top computer, tablet, or mobile phone and log in to their secure account at server 14 to answer security questions before a dose is dispensed.

The mixing value or ratio of liquid 1 (the active ingredient) and liquid 2 (the carrier or vehicle) is pre-set by the doctor at the start of treatment and may be modified as treatment progresses. In one example, liquid 1 may be methadone or another drug in liquid form, and liquid 2 may be a carrier or vehicle for the methadone such as propylene glycol (PG, aka peg 400), vegetable glycerol (VG), or coconut oil. The doctor determines how much methadone and carrier to administer to the patient at the start of treatment and this is stored in database 17 of the main processing system or server 14.

Figure 10:
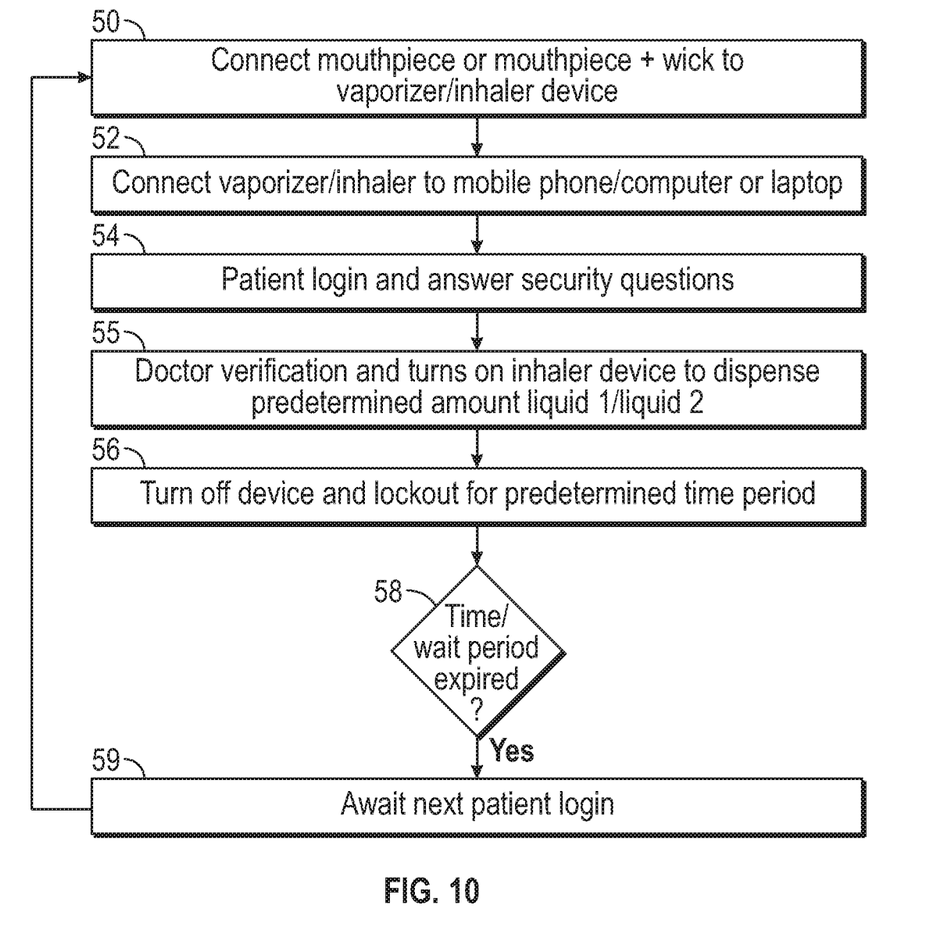
FIG. 10 is a flow diagram illustrating one embodiment of a method for controlling operation of the vaporization apparatus in the embodiments of FIGS. 2 to 9B when connected in the system of FIG. 1.

Device 12 can only be turned on at predetermined intervals dependent on the medication and the number of times per day it is to be administered, for example once a day. The control system software which controls operation of devices 12 in one embodiment is illustrated in FIG. 10. The program is set for a particular time and day and the patient schedules this for their daily online consultation, which may take place at a medical facility, at the patient's home, or other selected locations. Once the mouthpiece is connected to the container or e-vape box 24 (see step 50 of the software flow diagram of FIG. 10), as detected by a suitable sensor or switch 38, and the user connects the device to their selected user device 18 (step 52), a signal is sent via input/output device 34 to the main processing system or server 14 which can identify the box 24 and its location via the GPS or tracking device 46.

The patient logs in to their account using a user name and password. If the vaporization unit is not detected to be at an authorized location when the patient logs in (e.g. a clinic, the patient's home or work, or another predesignated location), a message may be sent to the user stating that the conditions for dispensing of a dose of medication have not been met, with a phone number for the user to call for more information. Assuming the device is detected to be at the authorized location, and the time period since the last dose is equal to or greater than the prescribed time period, the patient is prompted to answer a series of security questions to identify the patient (step 54), as well as questions set by the physician such as "How are you feeling today?", "Do you like inhalation methadone delivery as opposed to liquid oral form?". Answers are logged to data base (FIG. 1) 17 for further analysis. Once the questions are answered, the device is turned on, pumps 31 and 32 deliver the selected amounts of liquid 1 and liquid 2 to the heated wick, and the vaporized medication dose is delivered to the patient via mouthpiece 22 (step 55). Device 12 is then turned off and locked against further use for a predetermined period until the next medication dose is due (step 56). Once the lockout period expires (step 58), the system awaits the next patient log-in (step 60).

In the embodiment of FIGS. 2 and 3, when the engagement portion 40 of the mouthpiece device 22 is rotated or unthreaded out of locking engagement with the wick seat, spring loaded shutters or valves in the liquid inlets from pumps 31 and 32 return to a closed position. The pumps remain turned off for the entire lockout period, so that even if the patient re-engages the mouthpiece in the seat, no additional dose is dispensed. The used wick 28 may be re-used, or may be removed from the housing and disposed of in a hazardous waste container by medical personnel after each dose of medication. A new wick is installed before the device 12 is used again. Once a new wick is installed and the mouthpiece is again engaged in the container outlet port or seat for communication with the wick, the procedure of FIG. 10 can be repeated after the timed lockout period and patient log-in procedure. The tanks 26 and 27 contain enough medication and carrier liquid for multiple uses at predetermined intervals, and may be re-filled via the supply ports 49, as described above.

In the embodiment of FIGS. 2 and 3, the mouthpiece and wick are two separate entities. FIGS. 4 to 9B illustrate alternative embodiments in which a modified vaporization apparatus 70 has a combined mouthpiece and loadable or pre-loaded wick device 60 or 62 which is releasably attached to electronic vaporization unit 64 which is similar to unit 20 of the previous embodiment in the case of mouthpiece and wick device 60, or which comprises a modified housing or box containing no liquid supply tanks in the case of mouthpiece and pre-loaded wick device 62.

Figure 4:
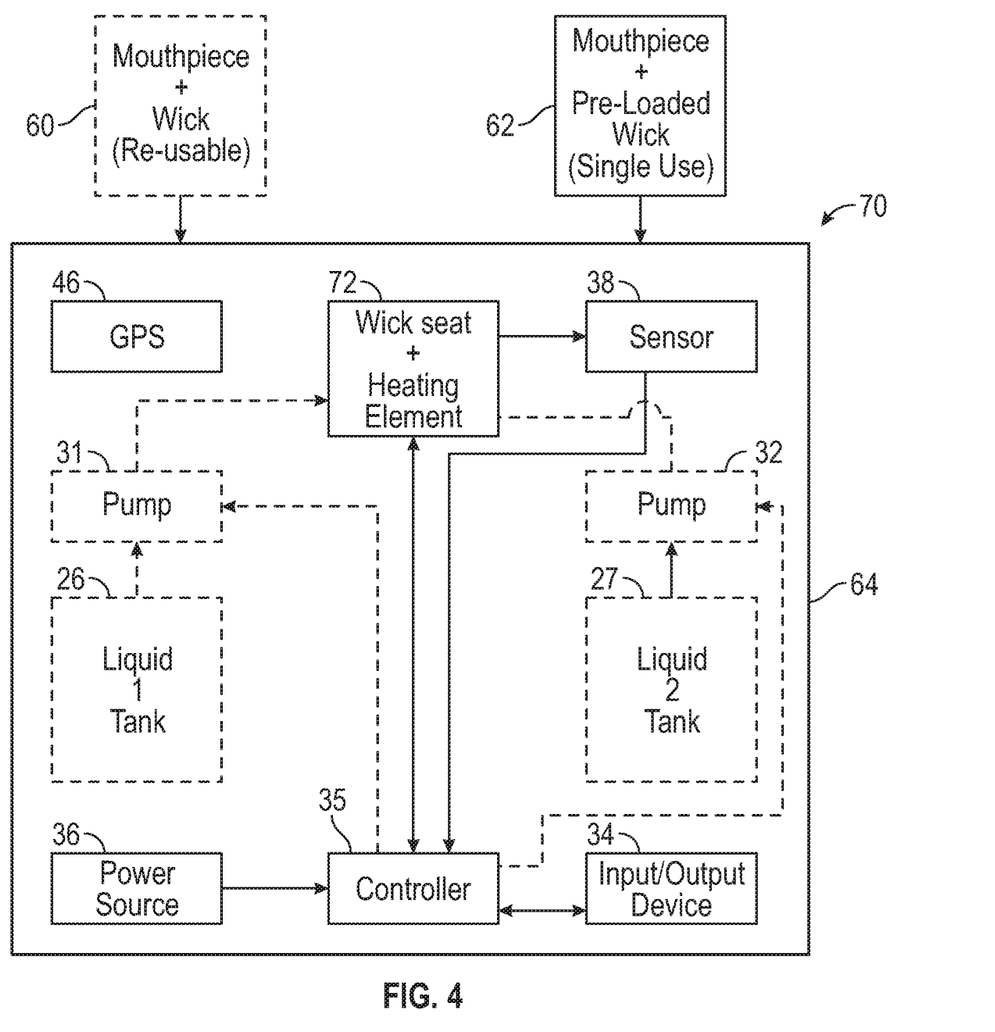
FIG. 4 is a block diagram similar to FIG. 2 but illustrating other embodiments of an inhalant delivery apparatus for use in the system of FIG. 1.
Figure 5:
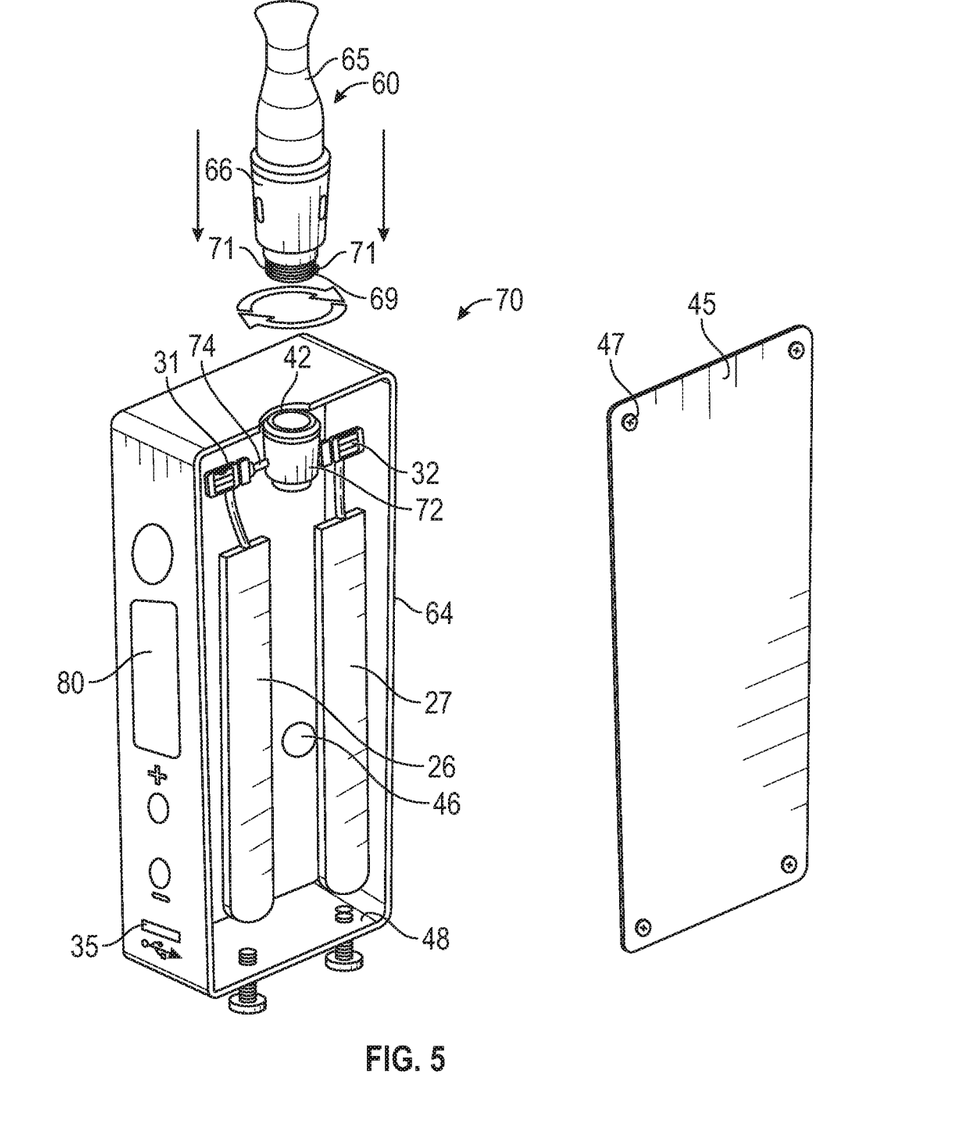
FIG. 5 illustrates the modified mouthpiece and wick device of FIG. 4 aligned for engagement in a mounting seat at the outlet port of the vaporization device of FIG. 4.
Figure 6:
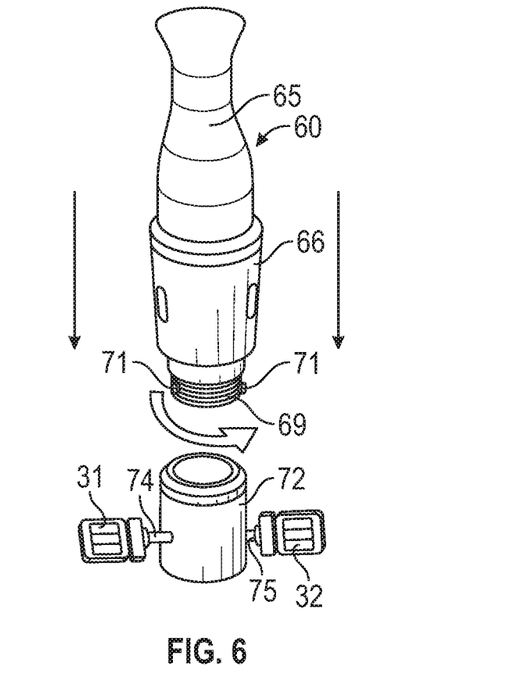
FIG. 6 is an enlarged view of the mouthpiece and wick device of FIG. 4 aligned with the mounting seat of FIG. 5 prior to engagement.

FIG. 4 illustrates the components inside housing or box 64 when used with a combined mouthpiece and loadable wick device 60 (see components in both solid and dotted outline) and with a combined mouthpiece and pre-loaded wick device 62 (see components in solid outline only). Some of the components inside box or container 64 are similar or identical to those of the first embodiment and like reference numbers are used for like parts as appropriate. However, instead of a wick inside the container as in FIGS. 2 and 3, wick device 60 includes both a mouthpiece 65 and a wick 66. The wick 66 has a threaded connecting portion 69 with diametrically opposite tubular connectors 71 which communicate with wick 66. Container or housing 64 has a seat 72 in communication with the outlet port 42 for receiving the threaded connection portion 69 and part of the wick 66, as indicated by the arrows in FIG. 5. Wick 66 includes a heating element (not illustrated).

Figure 8A:
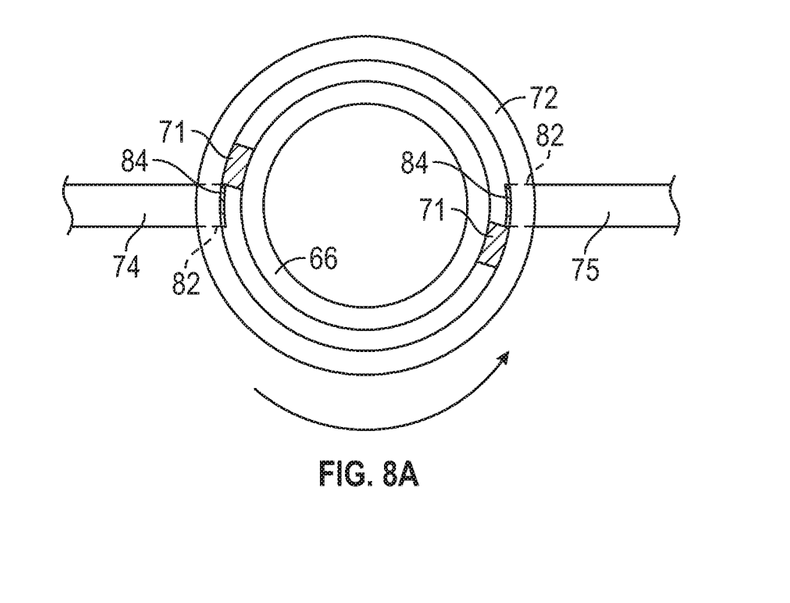
FIG. 8A is a horizontal cross-sectional view through the seat and inlet ports of FIG. 7 with the attachment portion of the mouthpiece device of FIGS. 4 to 7 engaged in the seat in a closed condition prior to twisting or rotating into the open condition.
Figure 8B:
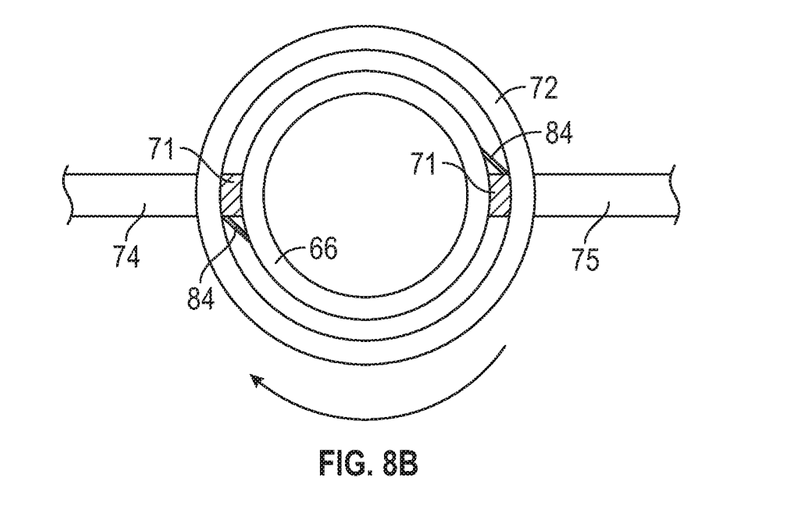
FIG. 8B is a horizontal cross-sectional view similar to FIG. 8A illustrating the mouthpiece device rotated into the open condition in which flapper or shutter valves normally closing and sealing the liquid inlets into the wick are pushed into the open position.
Figure 9A:
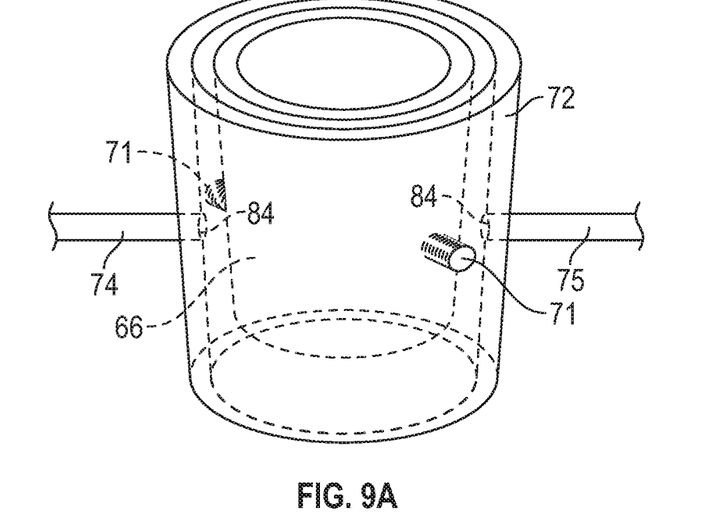
FIG. 9A is a front elevation, transparent or see-through view of the seat and engaged attachment portion of the mouthpiece in the closed or sealed condition of FIG. 8A.

As best illustrated in FIGS. 8A and 9A, liquid inlet ports 82 of seat 72 are in communication with the fluid delivery tubes 74, 75 and are closed by spring-loaded shutters or flapper valves 84 when the mouthpiece device is not connected in the inlet port or seat. When connecting portion 69 is initially inserted through the housing outlet port and into engagement in the seat, connectors 71 are offset from the liquid inlet ports 82 of tubes 74, 74, as seen in FIGS. 8A and 9A, in an annular space between the wick 66 and inner wall of seat 72. In order to lock the mouthpiece and wick device in place and open the shutters 84, the user rotates the mouthpiece device 60 in the direction of the arrow in FIG. 8A and the connectors 71 push the shutters 84 aside and move into alignment with ports 82, simultaneously compressing or loading shutter return springs 85 (see FIGS. 8B and 9B). This allows measured quantities of the two liquids in tanks 26 and 27 to be supplied to the wick 66 when a command signal is received from the remote processing system 14 to activate the pumps. The supplied mixture is thus vaporized for inhalation by the user via mouthpiece 65. The control system described above in connection with FIGS. 1 to 3 and 10 operates in the same way in this embodiment to control switching on and off of the liquid supply pumps when the mouthpiece and wick device is engaged in the seat.

Figure 9B:
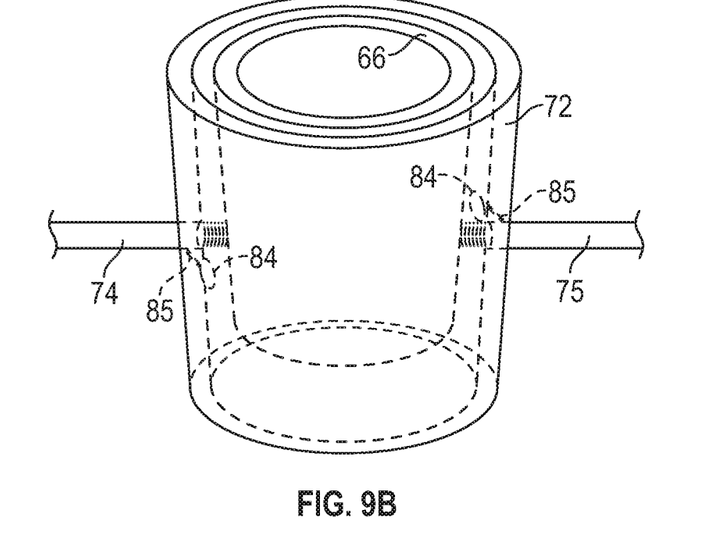
FIG. 9B is a front elevation view similar to FIG. 9A but illustrating the open position of FIG. 8B in which controlled amounts of the two liquids are supplied to the heated wick.

Once the patient receives a dose of vaporized medication from mouthpiece 65, the inhalant delivery pumps are switched off via a signal from server or processor 14 and mouthpiece/wick device 60 is rotated in the release direction indicated by the arrow in FIG. 8B, and removed from seat 72. This also moves the connectors 71 away from the shutters 84 and out of alignment with ports 82, back to the position shown in FIGS. 8A and 9A. The device cannot be removed from seat 72 until it is rotated back to this position, and must also be in this orientation in order to be inserted into the seat. Thus, the ports 82 are sealed and the interior of box or housing 64 is secure when the device 60 is removed. Appropriate notches or grooves for receiving the connectors 71 may be provided in the outlet port to ensure proper orientation of the connecting portion 69 in the position of FIGS. 8A and 9A when the device 60 is either inserted into the seat or removed from the seat at the end of a dose. Once the connectors 71 move away from the shutters, loaded springs 85 bias the shutters or flapper valves 84 back into the closed position of FIGS. 8A and 9A, shutting off the connection to the liquid supply tubes or passageways 74 and 75. The mouthpiece and wick are disposed of together in a hazardous waste container after use. The inhalant delivery device does not dispense a new dose until the timeout period has expired and a new mouthpiece and wick is inserted and rotated into the locked position in seat 72, as illustrated in FIGS. 8B and 9B.

In the alternative embodiment illustrated in FIG. 4, single-use combined mouthpiece and wick device 62 includes a mouthpiece similar or identical to that of device 62, and a wick which is pre-loaded with a mixture of medication and a carrier as prescribed by the physician. The patient may be provided with a selected number of mouthpieces with pre-loaded wicks in sterile packages for usage over a selected number of days. Device 62 is designed for engagement in a seat located at the outlet of a modified container or box 64 in the same manner as described above in connection with FIGS. 5 to 7, but in this case the box contains only the components shown in solid outline in FIG. 4. Since the wick in this embodiment is pre-loaded with the prescribed mixture of liquids, there is no need for any liquid holding tanks, pumps, or absorbent pad. In this case, the inhalant dispensing device does not dispense a dose of vaporized medication unless it is time for the next dose, a new mouthpiece with a pre-loaded wick 62 is inserted and in the locked position, and the patient connects the device to their computer or smart phone, logs in to the medication app, and answers the required questions, as in the previous embodiments. The combined mouthpiece and wick device 62 is discarded in a hazardous waste container after each use and the inhalant dispensing device is locked against use for a predetermined time period as selected by the prescribing physician, such as 24 hours.

Figure 7:
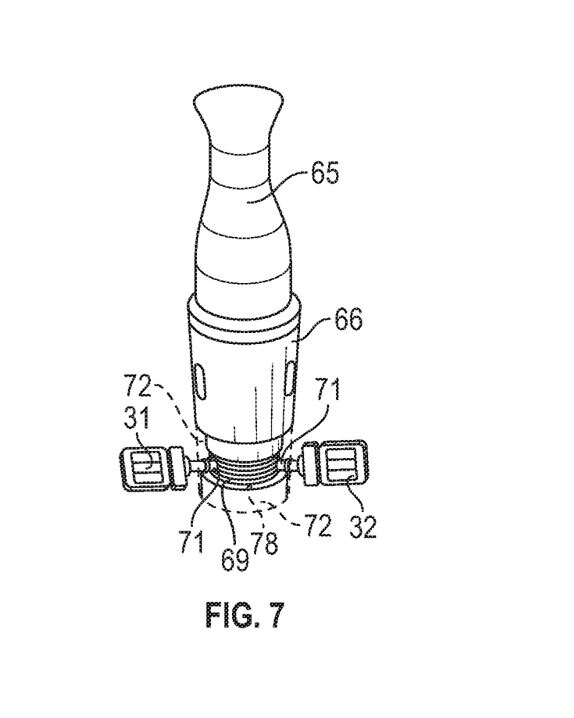
FIG. 7 illustrates the inlet or wick end of the mouthpiece device of FIGS. 4 and 5 engaged in the mounting seat and rotated into the operative position.

In one embodiment, a scale 78 is provided beneath the wick in the embodiment of FIGS. 2 to 4 and in the seat 72 in the embodiments of FIGS. 4 to 7, as indicated in dotted outline in FIG. 7. This allows the total weight of the mixed vehicle and medication to be measured and sent to the server or controller 14 for verification that appropriate mixing has taken place. The scale has a tare weight for each wick inserted in the device and the total weight may also be displayed on a digital output or display 80 on the box. This may also be arranged to alert the user if the mouthpiece/wick has not been inserted properly.

All of the inhalant dispensing devices described above are equipped with a tracking system and tracking data is relayed back to the central processor or server 14 for processing. In some embodiments, the user connects the device to either a computer or smart phone via a USB cord or wireless link and logs in to the drug dispensing control system prior to receiving a dose of inhaled medication. The system may be arranged to detect whether a user attempts to receive medication during the time out period and how many times they do so, and this is reported to medical personnel. The apparatus may be located in a clinic or taken outside the clinic for home use by the patient. The control software or computer program is set up to allow the physician to determine the vehicle to drug ratio each patient receives.

Although the mouthpiece device is connected to the electronic vaporization unit via a threaded engagement in the embodiments described above, other mating engagement formations such as relatively rotatable snap lock formations with release and secure positions may be used in alternative embodiments.

Figure 11:
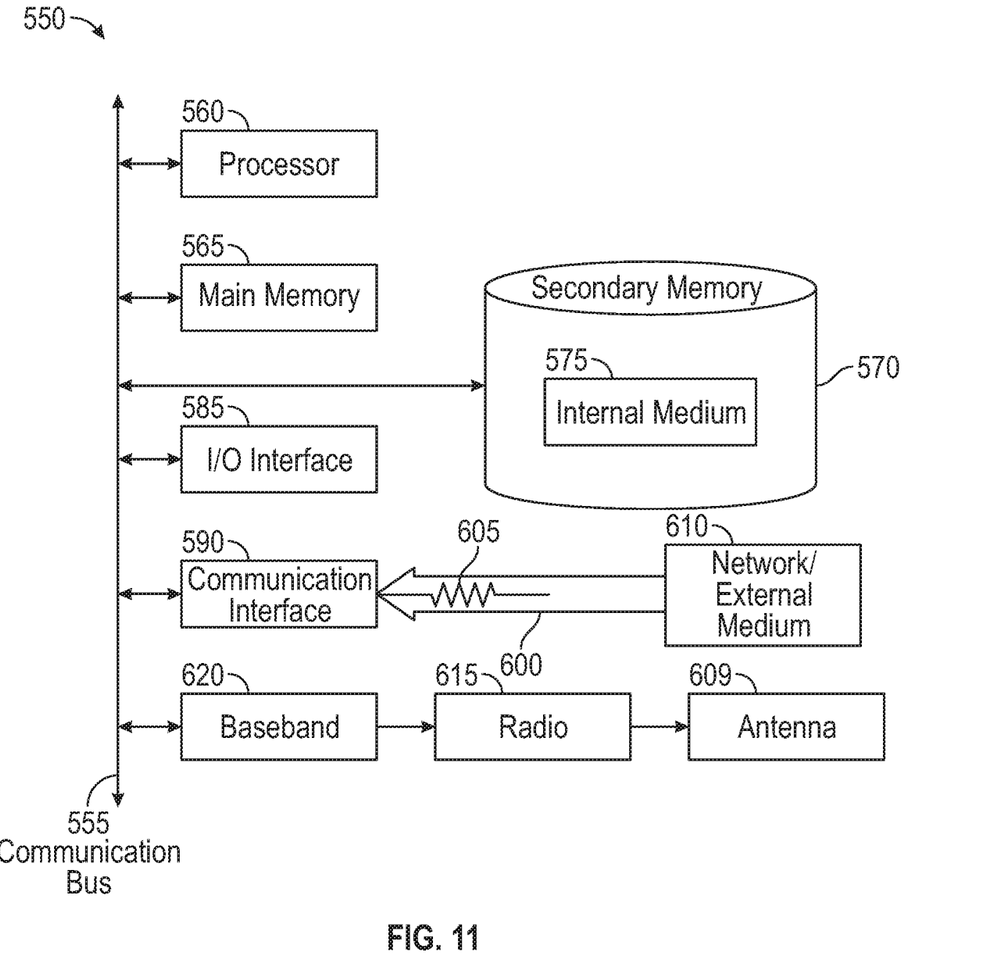
FIG. 11 is a block diagram illustrating an example processor based system that may be used in connection with various embodiments described herein.

FIG. 11 is a block diagram illustrating an example of a computer system 550 that may be used in connection with various embodiments described herein. For example, the computer system 550 may be used as the microprocessor or central processing unit 14 of FIG. 1 which receives status inputs from the hand held vaporization devices 12 or 70 and sends commands or control signals to those devices, and which communicates with physicians and patients who are logged on to the system, as described above. However, other computer systems and/or architectures may be used, as will be clear to those skilled in the art.

The computer system 550 preferably includes one or more processors, such as processor 560. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 560.

The processor 560 is preferably connected to a communication bus 555. The communication bus 555 may include a data channel for facilitating information transfer between storage and other peripheral components of the computer system 550. The communication bus 555 further may provide a set of signals used for communication with the processor 560, including a data bus, address bus, and control bus (not shown). The communication bus 555 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 550 preferably includes a data base containing main memory 565 and may also include a secondary memory 570. The main memory 565 provides storage of instructions and data in a computer readable medium for software programs executing on the processor 560, such as the software described above in connection with FIGS. 1 and 10. The main memory 565 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 570 may optionally include a hard disk drive 575 and/or a removable storage drive, for example a floppy disk drive, a magnetic tape drive, a compact disc ("CD") drive, a digital versatile disc ("DVD") drive, etc. The removable storage drive reads from and/or writes to a removable storage medium in a well-known manner. The removable storage medium may be, for example, a floppy disk, magnetic tape, CD, DVD, etc.

The removable storage medium is a non-transitory computer readable medium having stored thereon computer executable code (i.e., software) and/or data. The computer software or data stored on the removable storage medium is read into the computer system 550 as electrical communication signals for execution by the processor.

In alternative embodiments, secondary memory 570 may include other similar means for allowing computer programs or other data or instructions to be loaded into the computer system 550. Such means may include, for example, an external storage medium 610 and an interface 600. Examples of external storage medium 610 may include an external hard disk drive or an external optical drive, or an external magneto-optical drive.

Other examples of secondary memory 570 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units and interfaces, which allow software and data to be transferred from the removable storage unit to the computer system 550.

Computer system 550 may also include a communication interface 590. The communication interface 590 allows software and data to be transferred between computer system 550 and external devices such as user devices 18 and e-vape or electronic vaporization devices or units 12 or 70, printers, networks, or information sources. For example, computer software or executable code may be transferred to computer system 550 from a network server via communication interface 590. Examples of communication interface 590 include a modem, a network interface card ("NIC"), a communications port, a PCMCIA slot and card, an infrared interface, and an IEEE 1394 fire-wire, just to name a few. Communication interface may also comprise Bluetooth or other wireless communication interface.

Communication interface 590 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 590 are generally in the form of electrical communication signals 605. These signals are preferably provided to communication interface 590 via a communication channel 600. Communication channel 600 carries signals 605 and can be implemented using a variety of wired or wireless communication means including wire or cable, fiber optics, conventional phone line, cellular phone link, wireless data communication link, radio frequency ("RF") link, or infrared link, just to name a few.

Computer executable code (i.e., computer programs or software) is stored in the main memory 565 and/or the secondary memory 570. Computer programs can also be received via communication interface 590 and stored in the main memory 565 and/or the secondary memory 570. Such computer programs, when executed, enable the computer system 550 to perform the various functions of the embodiments described above.

In this description, the term "computer readable medium" is used to refer to any non-transitory computer readable storage media used to provide computer executable code (e.g., software and computer programs) to the computer system 550. Examples of these media include main memory 565, secondary memory 570 (including hard disk drive 575, removable storage medium, and external storage medium 610), and any peripheral device communicatively coupled with communication interface 590 (including a network information server or other network device). These non-transitory computer readable mediums are means for providing executable code, programming instructions, and software to the computer system 550.

In an embodiment that is implemented using software, the software may be stored on a computer readable medium and loaded into computer system 550 by way of removable storage drive 610, interface 585, or communication interface 590. In such an embodiment, the software is loaded into the computer system 550 in the form of electrical communication signals 605. The software, when executed by the processor 560, preferably causes the processor 560 to perform the features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

The system 550 also includes optional wireless communication components that facilitate wireless communication over a voice and over a data network. The wireless communication components may comprise an antenna system 609, a radio system 615 and/or a baseband system 620. In the communication device 550, radio frequency ("RF") signals, if generated, are transmitted and received over the air by the antenna system 609 under the management of the radio system 615.

In one embodiment, the antenna system 609, if present, may comprise one or more antennae and one or more multiplexers (not shown) that perform a switching function to provide the antenna system with transmit and receive signal paths. In the receive path, received RF signals can be coupled from a multiplexor to a low noise amplifier (not shown) that amplifies the received RF signal and sends the amplified signal to the radio system 615.

In alternative embodiments, the radio system 615 may comprise one or more radios that are configured to communication over various frequencies. In one embodiment, the radio system 615 may combine a demodulator (not shown) and modulator (not shown) in one integrated circuit ("IC"). The demodulator and modulator can also be separate components. In the incoming path, the demodulator strips away the RF carrier signal leaving a baseband receive audio signal, which is sent from the radio system 615 to the baseband system 620.

The baseband system 620 is also communicatively coupled with the processor 560. The central processing unit 560 has access to data storage areas 565 and 570. The central processing unit 560 is preferably configured to execute instructions (i.e., computer programs or software) that can be stored in the memory 565 or the secondary memory 570. Computer programs can also be received from the baseband processor 620 and stored in the data storage area 565 or in secondary memory, or executed upon receipt. Such computer programs, when executed, enable the computer system 550 to perform the various functions of the present invention as previously described. For example, data storage areas 565 may include various software modules (not shown) that perform the various functions of the present invention as previously described.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. An electronic vaporizer apparatus, comprising:
an electronic vaporization unit adapted to be hand held and having an outer housing with an outlet port, at least one liquid tank located in the outer housing, a seat communicating with the outlet port having a first fastener formation, a vaporization control signal processor, and an input/output communication device connected to the vaporization control signal processor and configured for communication with a remote server via a local user device;
a mouthpiece device separate from the electronic vaporization unit and having a mouthpiece at a first end configured for engagement by a user's mouth when inhaling a vapor and an engagement portion at a second end having a second fastener formation configured for releasable mating engagement with the first fastener formation in the seat to secure the mouthpiece device to the electronic vaporization unit; and
a wick for containing or receiving a liquid or mixture of liquids to be vaporized from the at least one liquid tank, the wick being mounted in the seat in the outer housing of the electronic vaporization unit or in the mouthpiece device, whereby the wick is located in the seat at least when the mouthpiece device is in releasable mating engagement with the seat;
whereby, on receipt of a control signal, which comprises information selecting an amount of liquid containing a medication, from the remote server received in part based on the mouthpiece device being in mating engagement with the seat in the electronic vaporization unit, the vaporization control signal processor is configured to control activation of the vaporizer apparatus to deliver the selected amount of the liquid containing the medication in the at least one liquid tank to the wick via at least one passageway for vaporization, and deliver a dose of vaporized medication to the mouthpiece,
wherein the at least one liquid tank comprises a first holding tank and a second holding tank located inside the outer housing for containing respective first and second liquids of the mixture of liquids to be mixed together and vaporized, wherein the at least one passageway comprises a first supply passageway between the first holding tank and the seat and a second supply passageway between the second holding tank and the seat, the first supply passageway comprising a first inlet port for supplying a controlled quantity of the first liquid from the first holding tank to the wick, and the second supply passageway comprising a second inlet port for supplying a controlled quantity of the second liquid from the second holding tank to the wick, the mouthpiece device comprises a first connector for supplying the controlled quantity of the first liquid from the first supply passage to the wick, and a second connector for supplying the controlled quantity of the second liquid from the second supply passage to the wick, the apparatus further comprising a first shutter or valve between the first supply passageway and the first connector and a second shutter or valve between the second supply passageway and the second connector, wherein the first shutter or valve and the second shutter or valve are configured to:

open in response to the mouthpiece device being in mating engagement with the seat in the electronic vaporization unit, thereby fluidly coupling the first and second supply passageways to the first and second connectors, respectively, and close when the mouthpiece device is not in mating engagement with the seat.

2. The apparatus of claim 1, further comprising a first pump for supplying the controlled quantity of the first liquid from the first holding tank to the wick via the first supply passageway, and a second pump for supplying the controlled quantity of the second liquid to the wick via the second supply passageway, wherein the vaporization control signal processor is configured to actuate the first and second pumps to supply predetermined amounts of said first and second liquids to the wick on receipt of the control signal from the remote server.

3. The apparatus of claim 1, wherein the control signal actuates pumps to supply the first and second liquids of the mixture of liquids to the wick.

4. The apparatus of claim 1, wherein the electronic vaporization unit detects that the mouthpiece device is in mating engagement with the seat, and receives the control signal in response to said detection.

5. The apparatus of claim 1, wherein the electronic vaporization unit is configured to be turned off by the vaporization control signal processor subsequent to the delivery of the dose of vaporized medication to the mouthpiece device and the electronic vaporization unit is configured to remain off until a prescribed time period has elapsed, wherein the prescribed time period is included in the control signal.

6. The apparatus of claim 1, wherein the control signal is received based, in part, on authorization of a current location of the electronic vaporizer apparatus based on a localization signal indicating the current location received by the remote server from the vaporization control signal processor.

7. The apparatus of claim 1, wherein the control signal is received based, in part, on a time period since a immediately preceding dose that is equal to or greater than a prescribed time period.

8. The apparatus of claim 1, wherein the control signal is received based, in part, on receipt of user answers to a plurality of security questions received by the vaporization control signal processor from the remote server.

9. A system comprising:
at least two electronic vaporization apparatuses each according to claim 1,
wherein a remote server is in communication with each of the at least two electronic vaporization apparatuses via one or more networks.

10. The system of claim 9, further comprising a remote processing device associated with a medical facility in communication with the at least two electronic vaporization apparatuses via the one or more networks.

* * * * *